US008545413B2

(12) United States Patent
Tao et al.

(10) Patent No.: US 8,545,413 B2
(45) Date of Patent: Oct. 1, 2013

(54) NON-CONTACT APPARATUS FOR MONITORING CARDIOPULMONARY ACTIVITY SIGNALS AND METHOD FOR THE SAME

(75) Inventors: Teh Ho Tao, Hsinchu (TW); Shih Jen Hu, Tainan County (TW); Su Chen Kuo, Miaoli County (TW); Jia Hung Peng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1235 days.

(21) Appl. No.: 11/954,586

(22) Filed: Dec. 12, 2007

(65) Prior Publication Data

US 2008/0146944 A1    Jun. 19, 2008

(30) Foreign Application Priority Data

Dec. 13, 2006  (TW) ................ 95146608 A

(51) Int. Cl.
*A61B 5/08* (2006.01)
*A61B 5/02* (2006.01)
*A61B 5/05* (2006.01)

(52) U.S. Cl.
USPC ........................ 600/484; 600/481; 600/427

(58) Field of Classification Search
None
See application file for complete search history.

(56) References Cited

U.S. PATENT DOCUMENTS

| 4,738,264 | A | | 4/1988 | Orlando et al. | |
|---|---|---|---|---|---|
| 4,958,638 | A | * | 9/1990 | Sharpe et al. | 600/407 |
| 5,105,354 | A | * | 4/1992 | Nishimura | 600/484 |
| 5,573,012 | A | | 11/1996 | McEwan | |
| 5,638,824 | A | | 6/1997 | Summers | |
| 5,964,720 | A | | 10/1999 | Pelz et al. | |
| 6,556,461 | B1 | * | 4/2003 | Khersonsky et al. | 363/41 |
| 2004/0070444 | A1 | * | 4/2004 | Pearson | 330/10 |
| 2004/0123667 | A1 | * | 7/2004 | McGrath | 73/704 |
| 2006/0217612 | A1 | | 9/2006 | Ouchi | |

FOREIGN PATENT DOCUMENTS

| GB | 2349759 | 8/2000 |
|---|---|---|
| WO | 94/20021 | 9/1994 |
| WO | 2005/092190 | 10/2005 |
| WO | 2007/143535 | 12/2007 |

OTHER PUBLICATIONS

Office Action dated Mar. 15, 2010 for 200610170013.9 which is the corresponding Chinese application that cites US5638824A, Summarized Translation.
Chinese Office Action dated Sep. 22, 2011 for 200610170013.9, which is a corresponding Chinese application, that cites US2008/217612.

* cited by examiner

*Primary Examiner* — Anne Gussow
*Assistant Examiner* — Channing S Mahatan
(74) *Attorney, Agent, or Firm* — WPAT, P.C.; Anthony King

(57) ABSTRACT

A non-contact apparatus for monitoring cardiopulmonary activity signals comprises a pulse-series generator configured to generate a series of probing pulses and a series of reference pulses, a transmitting antenna configured to emit the probing pulses to a chest portion and a series of scattered pulses generated from the probing pulses by the scattering of the chest portion, a receiving antenna configured to receive the scattered pulses, a mixer including a first input port configured to receive the reference pulses and a second input port electrically connected to the receiving antenna and a signal-processing module configured to generate cardiopulmonary activity signals after the scattered pulses and the reference pulses are processed by the mixer.

8 Claims, 8 Drawing Sheets

NON-CONTACT APPARATUS FOR MONITORING CARDIOPULMONARY ACTIVITY SIGNALS AND METHOD FOR THE SAME

BACKGROUND OF THE INVENTION

The present invention relates to a technology for monitoring cardiopulmonary activity signals, and more particularly, to a non-contact apparatus and method for monitoring cardiopulmonary activity signals Breathing disorders commonly occur in premature infants, which manifest themselves in symptoms such as apnea or intermittent breathing etc., and can further develop into two types of complications: one of which occurs with apnea of premature birth infants, also known as apnea of prematurity (AOP); the other is sudden infant death syndrome (SIDS) or apparent life threatening event (ALTE). If AOP is not properly diagnosed and treated, premature infants diagnosed with this type of symptom will be highly susceptible to SIDS and are accident-prone at home. Cessation of breathing might lead to hemodynamic chain reactions such as slowdown of the heartbeat rate, and even lowered blood pressure. These changes in hemodynamics can induce temporary loss of blood and oxygen to critical organs, especially to the brain cells and may even cause permanent damage to them. In clinical trials, premature infants often become stable in all other aspects and could be discharged from the hospital, if it were not for this type of irregular apnea symptom.

Infant monitors currently in clinical use are based on traditional bedside monitors of patients' physical condition and use three electrodes attached to the skin of the infant's chest, acquiring the signals from the changes in the chest impedance by breathing and heartbeat signals; these two signals are then converted into the separate breathing frequency and heartbeat rate by the filter. A major drawback of this type of monitoring technology is that prolonged contact with the sensor plates will cause skin redness, sensitivity, or deterioration; furthermore, monitors used clinically are often expensive and therefore not suitable for home caretaking purposes.

To solve the above-mentioned problem, U.S. Pat. No. 4,738,264 disclosed a vibration measurement apparatus that is separated from the patient and is disposed on the bed. The main principle behind the apparatus is that tiny vibrations of the body surfaces from normal breathing and heartbeat are transferred to the measurement apparatus through the bed, and then the apparatus converts the signals into a comprehensive energy index to represent the infant's breathing and heartbeat conditions. The drawback of this technique is that it cannot accurately distinguish and measure the infant's breathing frequency and heartbeat rate, and therefore cannot fulfill the clinical requirements for detecting the AOP alert threshold (i.e. breathing frequency is less than 20/minute of breathing ceases for over 15 seconds, and heartbeat rate is less than 80/minute).

In addition, U.S. Pat. No. 5,964,720 disclosed a distributed vibration measurement system that uses the piezoelectric crystals as the vibration sensors and uses strips of conducting film as the base of the sensors. These conductive strips can be embedded in the bed mattresses, seat backs, or cushions to detect tiny vibrations of the body surface resulting from normal breathing and the heartbeat of the patient. The major drawback of this technique is that the heart and chest vibration signals captured by the sensors tend to be subject to interference from vibration noise from the surroundings that travel through the human body and bed or seat to the sensor.

SUMMARY OF THE INVENTION

One exemplary example consistent with the present invention provides a non-contact apparatus for monitoring cardiopulmonary activity signals using a series of high-frequency sinusoidal pulses to detect cardiopulmonary activity signals such as the heartbeat and breathing.

A non-contact apparatus for monitoring cardiopulmonary activity signals according to this example of the present invention comprises a pulse-series generator configured to generate a series of probing pulses and a series of reference pulses, a transmitting antenna configured to transmit the probing pulses to a chest portion and a series of scattered pulses being generated from the probing pulses by the scattering of the chest portion, a receiving antenna configured to receive the scattered pulses, a mixer including a first input port configured to receive the reference pulses and a second input port electrically connected to the receiving antenna to receive scattered pulses, and a signal-processing module configured to generate the cardiopulmonary activity signals after the scattered pulses and the reference pulses are processed by the mixer.

Another exemplary example consistent with of the present invention provides a method for acquiring cardiopulmonary activity signals comprising the steps of transmitting probing pulses to the chest portion to generate scattered pulses from the probing pulses by the scattering of the chest portion, generating a phase-difference signal between the scattered pulses and reference pulses by a mixer, converting the phase-difference signal into a digital signal representing the cardiopulmonary activity signal, and checking to determine if the cardiopulmonary activity is normal and generating an alarm signal if the checking result is negative.

A further exemplary example consistent with of the present invention provides a method for acquiring cardiopulmonary activity signals comprising the steps of transmitting probing pulses to a chest portion to generate scattered pulses from the probing pulses by the scattering of the chest portion, generating a phase-difference signal between the scattered pulses and reference pulses by a mixer, converting the phase-difference signal into a digital signal representing the cardiopulmonary activity, and calculating the frequency of the cardiopulmonary activity based on the digital signal.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
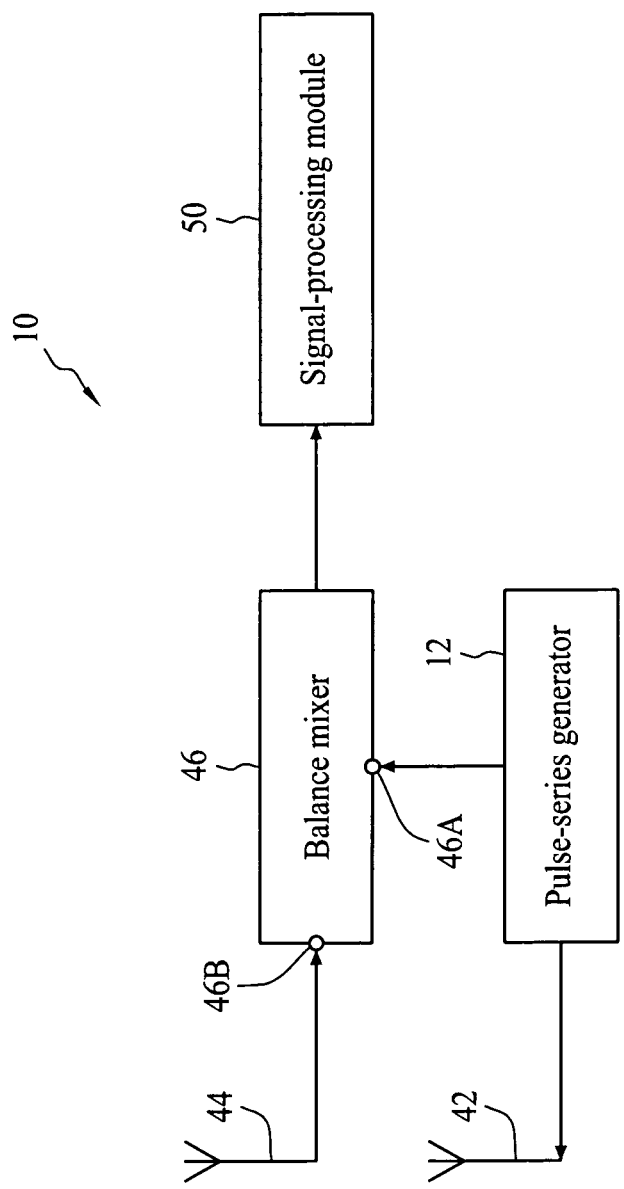
FIG. 1 illustrates the functional block diagram of a non-contact apparatus for monitoring cardiopulmonary activity signals according to one embodiment of the present invention.

FIG. 1 illustrates the functional block diagram of a non-contact apparatus 10 for monitoring cardiopulmonary activity signals according to one embodiment of the present invention. The non-contact apparatus 10 comprises a pulse-series generator 12 configured to generate a series of high-frequency sinusoidal probing pulses and reference pulses, a transmitting antenna 42 configured to emit the probing pulses to the chest portion to generate a series of scattered pulses from the probing pulses by the scattering of the chest portion, a receiving antenna 44 configured to receive the scattered pulses by the chest portion, a balance mixer 46 having a first input port 46A configured to receive the reference pulses and a second input port 46B electrically connected to the receiving antenna 44 to receive scattered pulses, and a signal-processing module 50 configured to generate the cardiopulmonary activity signals after the scattered pulses and the reference pulses are mixed by the balance mixer 46.

Figure 2:
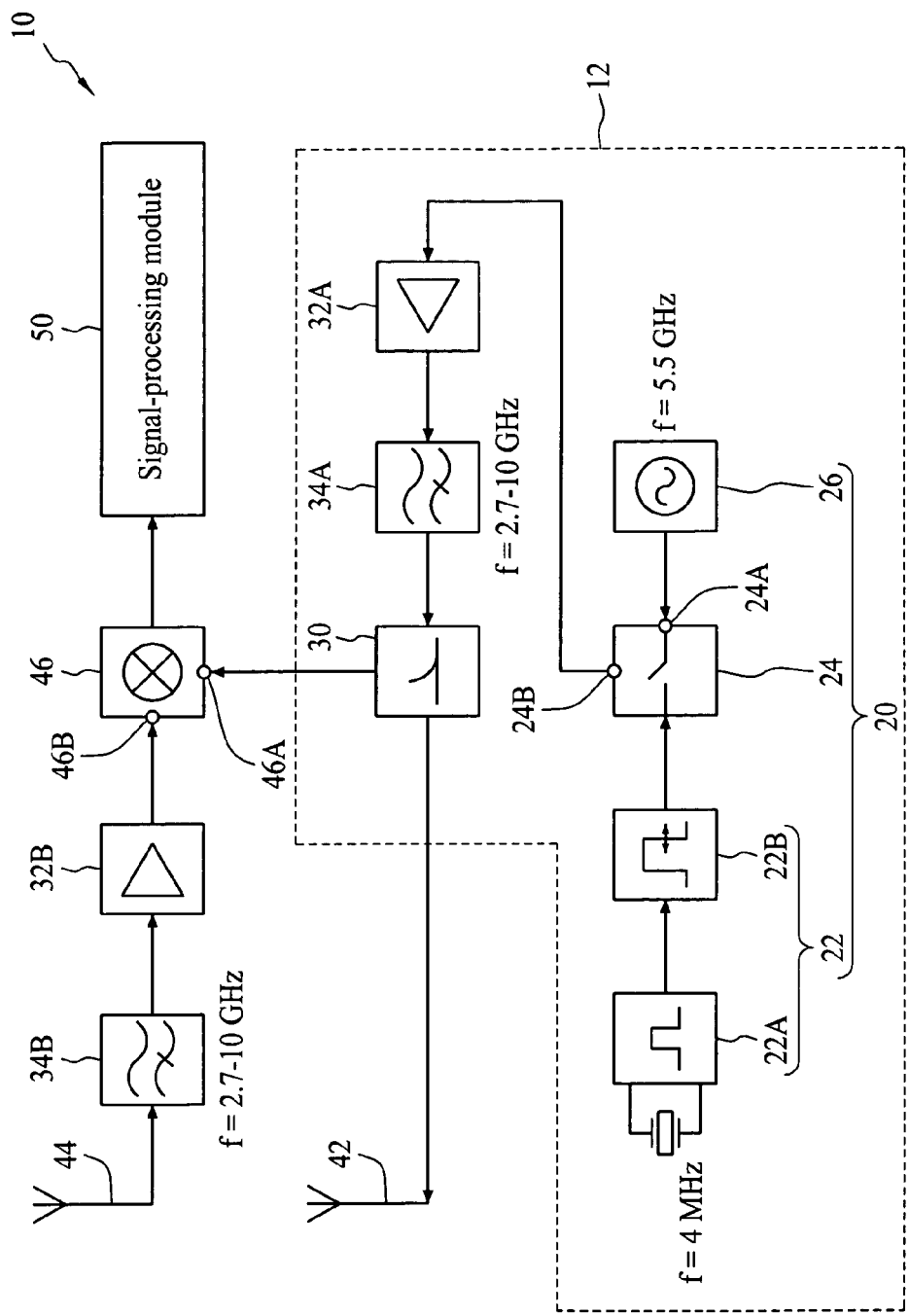
FIG. 2 illustrates the system architecture of the non-contact apparatus according to one embodiment of the present invention.

FIG. 2 illustrates the system architecture of the non-contact apparatus 10 according to one embodiment of the present invention. The pulse-series generator 12 comprises a pulse generator 20 configured to generate a series of high-frequency sinusoidal pulses, from which the probing pulses and the reference pulses are generated by the splitter 30 such as a Wilkinson splitter coupled to the high-frequency filter 34A. The pulse generator 20 comprises a sinusoidal-signal generator 26 configured to generate a 5.5 GHz continuous sinusoidal signal, a switching-signal generator 22 configured to generate a switching signal, and a switching device 24 having an input port 24A and an output port 24B and configured to turn on according to the switching signal such that the continuous sinusoidal signal can pass through the switching device 22 to form the high-frequency sinusoidal pulses. The switching-signal generator 22 comprises a clock generator 22A configured to generate a clock signal, and a waveform shaper 22B configured to adjust the time interval, 6.0 ns nominal, of the clock signal to generate the switching signal.

Figure 3:
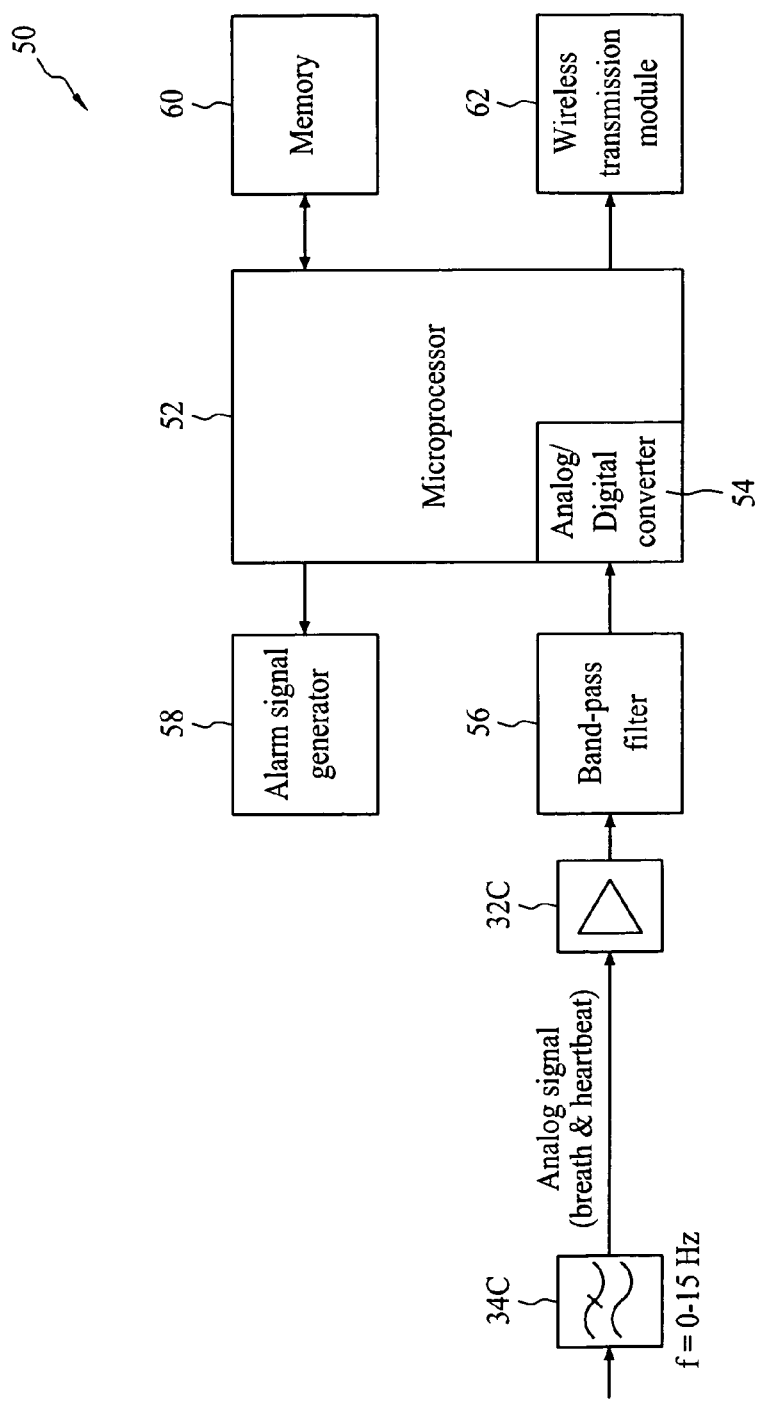
FIG. 3 illustrates the functional block diagram of the signal-processing module according to one embodiment of the present invention.

The non-contact apparatus 10 further comprises a first amplifier 32A electrically coupled to the output port of the pulse generator 20, a first high-frequency filter 34A electrically coupled to the first amplifier 32A and the splitter 30, a second high-frequency filter 34B electrically coupled to the receiving antenna 44, and a second low noise amplifier 32B electrically coupled to the second high-frequency filter 34B and the balance mixer 46. FIG. 3 illustrates the functional block diagram of the signal-processing module 50 according to one embodiment of the present invention. The signal-processing module 50 comprises a low-frequency filter 34C electrically coupled to the output port of the balance mixer 46, a third amplifier 32C electrically coupled to the low-frequency filter 34C, a band-pass filter 56 electrically coupled to the third amplifier 32C, a microprocessor 52 with a built-in analog/digital converter 54 electrically coupled to the band-pass filter 56, an alarm signal generator 58, a memory unit 60 configured to store data, and a wireless transmission module 62.

The signal-processing module 50 serves to output the analog signal representing breathing or heartbeat, and the analog/digital converter 54 then converts the analog signal into a digital signal. The breathing or heartbeat signals can be extracted from the digital signal by the firmware of the microprocessor 52, and the breathing frequency or heartbeat rate can be calculated with a certain signal-processing algorithm. The alarm signal generator 58 is configured to send an alarm signal when there is an anomaly, and the processed signals can be sent through the wireless transmission module 62 to the data server for further statistical analysis, printing, and storage.

Figure 4:
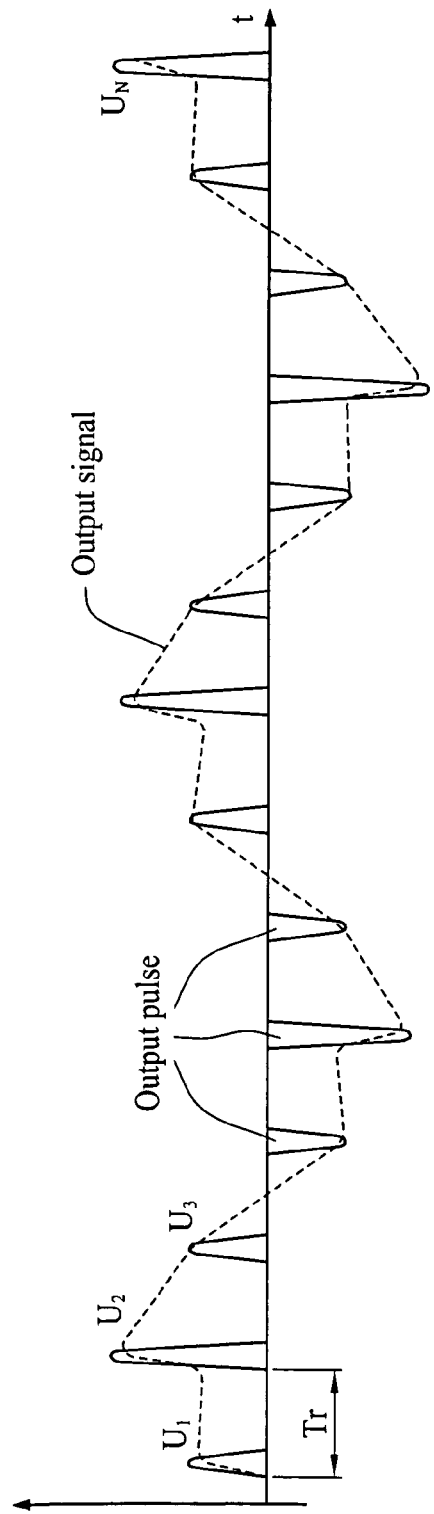
FIG. 4 illustrates the output signals of the balance mixer according to one embodiment of the present invention.

FIG. 4 illustrates the output signals of the balance mixer 46 according to one embodiment of the present invention. The high-frequency sinusoidal pulses are filtered by the first high-frequency filter 34A and then split into two parts by the splitter 30; one is the probing pulses transmitted to the chest portion by the transmitting antenna 42 and the other is the reference pulses fed into the first input port 46A of the balance mixer 46. The transmitted high-frequency sinusoidal probing pulses are then scattered by the chest portion of the subject to generate the scattered pulses, which is then received by the receiving antenna 44. Subsequently, the scattered pulses are mixed with the high-frequency sinusoidal reference pulses by the balance mixer 46. The output of the balance mixer 46 is a series of high-frequency pulses, with the polarity and amplitude of each pulse corresponding to the phase difference of the scattered pulses and the reference pulses. The low-frequency filter 34C will capture the envelop (the dotted lines in FIG. 4) of the high-frequency pulses to obtain the breathing and heartbeat signals of the patient, while the third amplifier 32C will magnify the amplitude of the signal and the band-pass filter 56 further removes baseline drift and high frequency noises.

Figure 5:
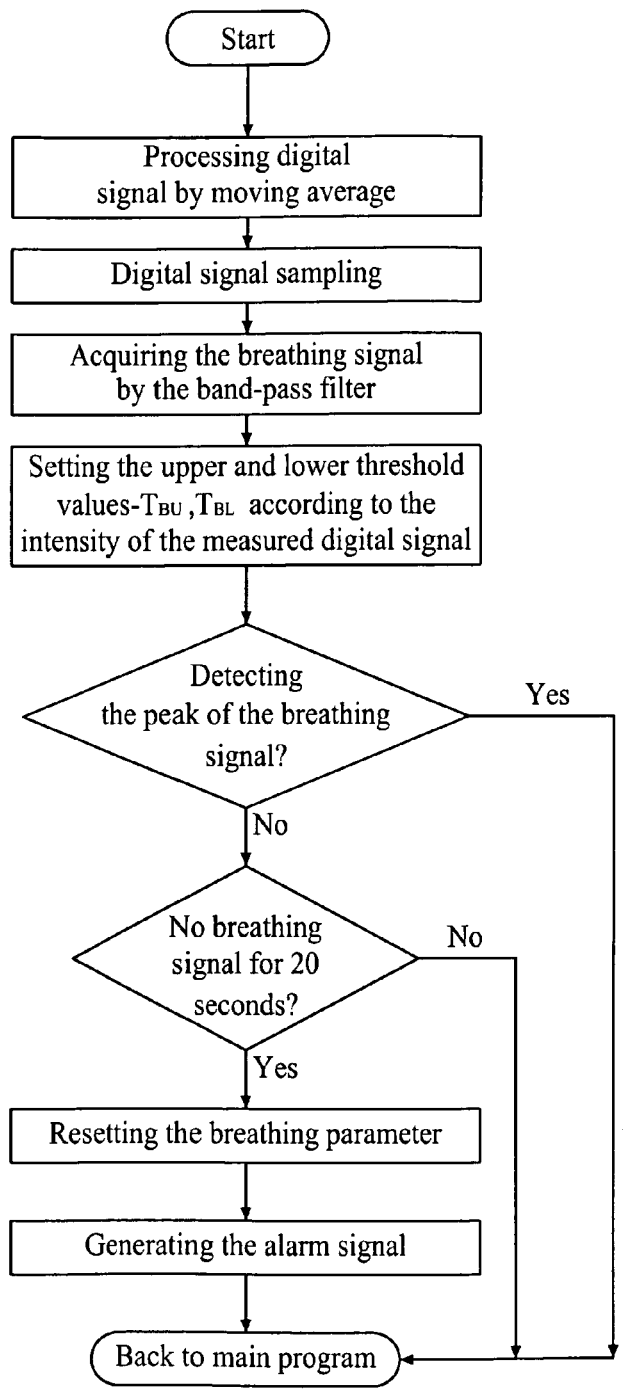
FIG. 5 illustrates a method for processing the digital signal after it is generated by the mixer according to one embodiment of the present invention.
Figure 6:
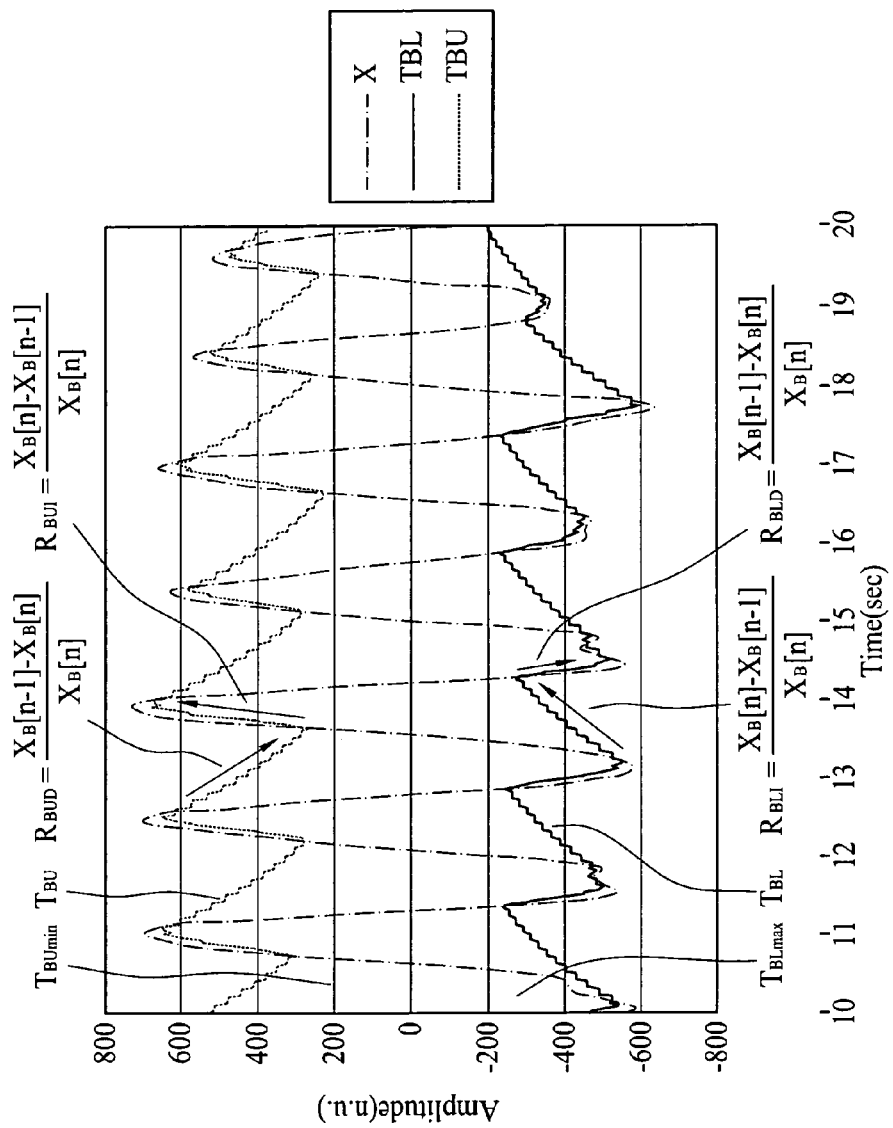
FIG. 6 illustrates cardiopulmonary activity signals according to one embodiment of the present invention.

FIG. 5 illustrates a method for processing the digital signal after it is generated by the mixer 46 according to one embodiment of the present invention. The moving average method is used to reduce the high frequency noise. A band-pass filter with −3 dB bandwidth from 0.1 Hz to 0.5 Hz is employed to reduce the noise outside the range of subject's normal range of breathing. To set-up the threshold values, the minimum of the upper threshold value ($T_{BUmin}$) and the maximum of the lower threshold value ($T_{BLmax}$), are first defined as two times of the magnitude of the background noise. For example, if the background noise is between −100~100, then the $T_{BUmin}$ is 200 and $T_{BLmax}$ is −200. Then the upper threshold value ($T_{BU}$) and the lower threshold ($T_{BL}$) are adjusted as shown in FIG. 6. If the signal value $X_B[n]$ is larger than $T_{BU}[n]$, the value of $T_{BU}[n+1]$ is increased with ratio $R_{BUI}$.

$$T_{BU}[n+1]=(1+R_{BUI})*T_{BU}[n]$$

Where $R_{BUI}=(X_B[n]-X_B[n-1])/X_B[n]$

If the signal value $X_B[n]$ is smaller than $T_{BU}[n]$, the upper threshold value $T_{BU}[n+1]$ is then reduced with ratio $R_{BUD}$.

$$T_{BU}[n+1]=(1-R_{BUD})*T_{BU}[n]$$

Where $R_{BUD}=(X_B[n-1]-X_B[n])/X_B[n]$

Similarly, if the signal value is less than the lower threshold, the lower threshold is reduced with ratio $R_{BLD}$.

$$T_{BL}[n+1]=(1-R_{BLD})*T_{BL}[n]$$

Where $R_{BLD}=(X_B[n-1]-X_B[n])/X_B[n]$

If the signal value is higher than the lower threshold, the lower threshold is then increased with ratio $R_{BLI}$.

$$T_{BL}[n+1]=(1+R_{BLI})*T_{BL}[n]$$

Where $R_{BLI}=(X_B[n]-X_B[n-1])/X_B[n]$

Subsequently, the intensity of the measured digital signal is compared with thresholds to check whether a signal peak representing the breathing activity is detected. If the signal is larger than $T_{BU}$, the "peak searching procedure" begins to record the location of current maximum value. The location would be continuously updated until the signal lower than $T_{BL}$. If there is no digital signal with intensity greater than $T_{BU}$ for a predetermined time (for example, 20 seconds), an alarm signal will be generated and all breathing parameters will be reset to zero to restart the calculation process.

Figure 7:
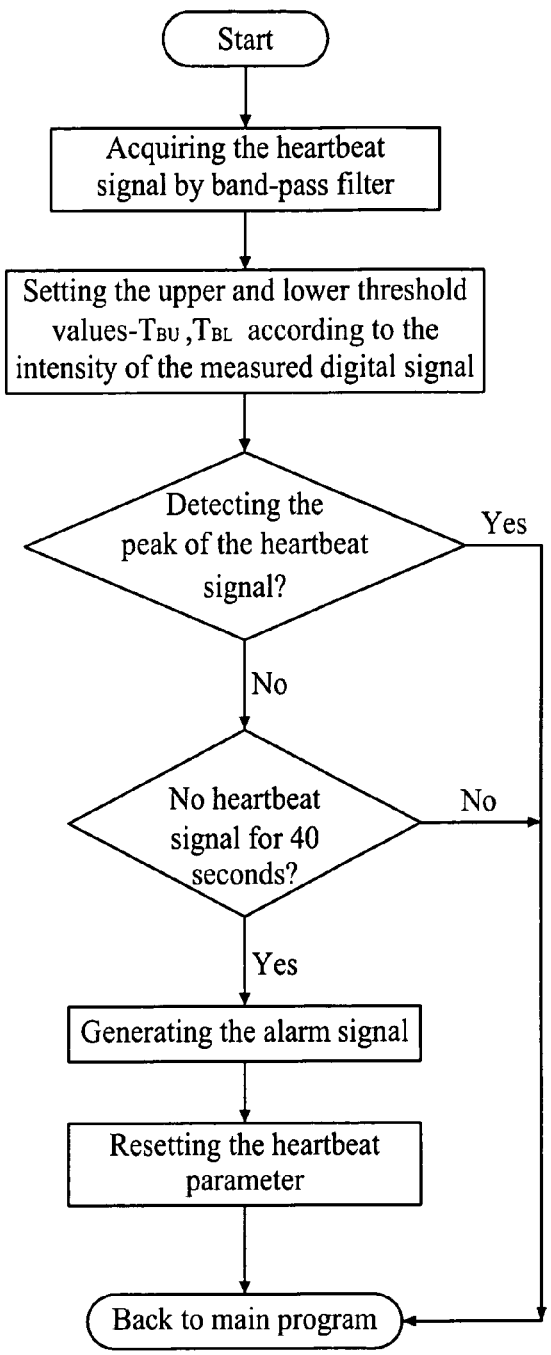
FIG. 7 illustrates a method for acquiring cardiopulmonary activity signals according to the another embodiment of the present invention.

FIG. 7 illustrates a method for acquiring cardiopulmonary activity signals according to another embodiment of the present invention, in which an alarm signal will be sent when the heartbeat is irregular. The digital signals captured by the non-contact apparatus 10 are heartbeat signals, while the alarm signal represents the cessation of the heartbeat. The microprocessor 52 of the signal-processing module 50 is configured to filter out the heartbeat signal through a band-pass filter with −3 dB bandwidth from 0.7 Hz to 2.5 Hz that is implemented in the software, and then set thresholds according to the empirical value or the intensity of the measured digital signal. The "peak searching procedure" is the same as that in breathing signal detection.

Figure 8:
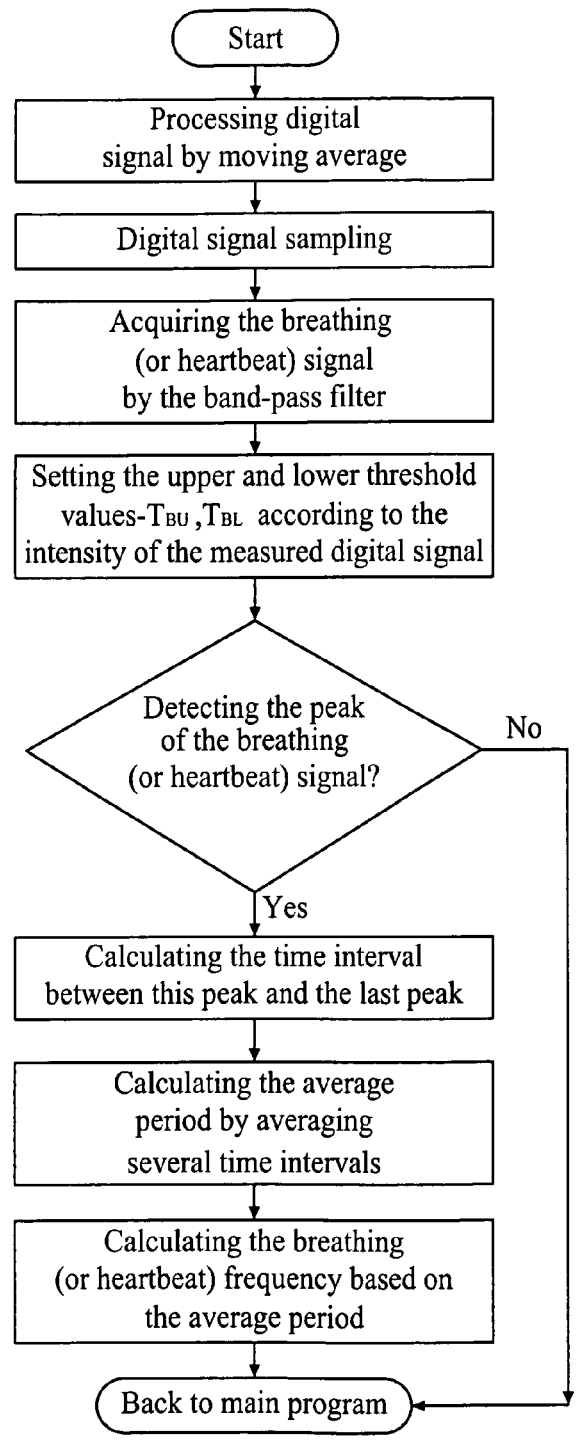
FIG. 8 illustrates a method for measuring the breathing frequency (heartbeat rate) of a patient according to one embodiment of the present invention.

FIG. 8 illustrates a method for measuring the breathing frequency (heartbeat rate) of a patient according to one embodiment of the present invention. The digital signal processing is the same as previous procedure and then peak detecting is performed to record location of each peak. When the peak of the breathing (heartbeat) signals is detected, the time interval between the current breathing (heartbeat) peak and the previous breathing (heartbeat) peak is calculated and saved to the memory 60. The time intervals between a plurality signal peaks are averaged to obtain the average interval, and the breathing frequency (heartbeat rate) is calculated by using the average interval. Furthermore, the present invention can selectively capture a portion of the digital signal (for example setting the sampling rate at ⅓) or discard unstable signals during system startup stage after applying the moving average method to the data signal.

After the calculation of the breathing frequency (heartbeat rate) is completed, the breathing frequency (heartbeat rate) is checked to determine whether it falls in a predetermined range. If the calculated breathing frequency (heartbeat rate) is higher than the predetermined range, an alarm signal indicating the breathing frequency (heartbeat rate) is too high is generated; in contrast, if the calculated breathing frequency (heartbeat rate) is lower than the predetermined range, an alarm signal indicating the breathing frequency (heartbeat rate) is too low is generated.

The above-described embodiments of the present invention are intended for illustration purposes only. Numerous alternative embodiments may be devised by those skilled in the art without departing from the scope of the following claims.

What is claimed is:

1. A non-contact apparatus for monitoring cardiopulmonary activity signals, comprising:
    a pulse-series generator configured to generate a series of probing pulses and a series of reference pulses, comprising:
        a sinusoidal-signal generator configured to generate a continuous sinusoidal signal;
        a switching-signal generator configured to generate a switching signal comprising:
            a clock generator configured to generate a clock signal; and
            a waveform shaper configured to adjust the time interval of the clock signal to generate the switching signal; and
        a switching device configured to turn on according to the switching signal such that the continuous sinusoidal signal can pass through the switching device to form high-frequency sinusoidal pulses;
    a transmitting antenna configured to transmit the probing pulses to a chest portion, wherein the chest portion scatters the probing pulses to generate a series of scattered pulses;
    a receiving antenna configured to receive the scattered pulses;
    a mixer including a first input port configured to receive the reference pulses and a second input port electrically connected to the receiving antenna to receive the scattered pulses; and
    a signal-processing module configured to generate the cardiopulmonary activity signals after the scattered pulses and the reference pulses are processed by the mixer,
    wherein the transmitting antenna and the receiving antenna are separate antennas.

2. The non-contact apparatus for monitoring cardiopulmonary activity signals of claim 1, wherein the pulse-series generator includes:
    a pulse generator configured to generate a series of high-frequency sinusoidal pulses; and
    a splitter coupled to the pulse generator and configured to generate the probing pulses and the reference pulses from the high-frequency sinusoidal pulses.

3. The non-contact apparatus for monitoring cardiopulmonary activity signals of claim 2, further comprising:
    an amplifier electrically connected to an output port of the pulse generator; and
    a high-frequency filter electrically connected to the amplifier and the splitter.

4. The non-contact apparatus for monitoring cardiopulmonary activity signals of claim 1, further comprising:
    a high-frequency filter electrically connected to an output port of the receiving antenna; and
    a low noise amplifier electrically connected to the high-frequency filter and the mixer.

5. The non-contact apparatus for monitoring cardiopulmonary activity signals of claim 1, further comprising:
    a low-frequency filter electrically connected to an output port of the mixer;
    an amplifier electrically connected to an output port of the low-frequency filter; and
    a band-pass filter electrically connected to the output port of the amplifier for reducing noise outside a subject's normal range of breathing or heartbeat, wherein the band-pass filter comprises a plurality of threshold values, a minimum of a upper threshold value and a maximum of a lower threshold value, are first defined as two times of a magnitude of a background noise.

6. The non-contact apparatus for monitoring cardiopulmonary activity signals of claim 1, wherein the signal-processing module includes a microprocessor having an analog/digital converter configured to convert the cardiopulmonary activity signals into digital signals, wherein the microprocessor of the signal-processing module is configured to filter out breathing or heartbeat signals that is implemented in a software.

7. The non-contact apparatus for monitoring cardiopulmonary activity signals of claim 6, wherein the signal-processing module further includes an alarm signal generator electrically connected to the microprocessor.

8. The non-contact apparatus for acquiring cardiopulmonary activity signals of claim 1, wherein the mixer is a balance mixer.

* * * * *